(12) United States Patent
Dempf et al.

(10) Patent No.: US 6,310,258 B1
(45) Date of Patent: Oct. 30, 2001

(54) PROCESS FOR PREPARING 1,3-DIKETONES

(75) Inventors: Dominik Dempf, Burghausen; Thomas List, Neumarkt St. Veit; Wolfgang Deinhammer, Burghausen, all of (DE); Georges Heyen, Embourg (BE)

(73) Assignee: Wacker Chemie GmbH (DE)

( * ) Notice: Subject to any disclaimer, the term of this patent is extended or adjusted under 35 U.S.C. 154(b) by 0 days.

(21) Appl. No.: 09/628,624

(22) Filed: Jul. 31, 2000

(30) Foreign Application Priority Data

Aug. 13, 1999 (DE) .............................................. 199 38 341

(51) Int. Cl.$^7$ .................................................... C07C 45/67
(52) U.S. Cl. ............................................ 568/383; 568/384
(58) Field of Search ..................................... 568/383, 384

(56) References Cited

U.S. PATENT DOCUMENTS 2,395,800  3/1946  Boese et al. .
3,794,686  2/1974  Spes et al. .

FOREIGN PATENT DOCUMENTS 2 047 320   3/1972  (DE) .
63-159337   7/1988  (JP) .

OTHER PUBLICATIONS

Derwent Abstract corresponding to JP–A 63159337 AN 1988–224238[32].

"Conversion Of Ketone Enol Esters To Beta–Diketones By Intramolecular Thermal Rearrangement And By Intermolecular Acylations Using Boron Fluoride", 1950, p. 3635–3642.

*Primary Examiner*—Johann Richter
*Assistant Examiner*—Sikarl A. Witherspoon
(74) *Attorney, Agent, or Firm*—Brooks & Kushman P.C.

(57) ABSTRACT

The invention provides a process for preparing 1,3-diketones by rearrangement of the isomeric enol ester in a tube reactor comprising a heated portion and an unheated insulated portion which can optionally be provided with cooling means. The unheated portion of the reactor has a higher volume to surface ratio than the heated portion of the reactor. The reaction can be carried out adiabatically in the unheated portion of the reactor. The process and apparatus provide higher yields and selectivity to the 1,3-diketones.

17 Claims, 1 Drawing Sheet

PROCESS FOR PREPARING 1,3-DIKETONES

FIELD OF THE INVENTION

The invention relates to a process for preparing 1,3-diketones by thermal rearrangement of the corresponding isomeric enol esters, and also to an apparatus for carrying out the process.

BACKGROUND OF THE INVENTION

It is known from U.S. Pat. No. 2,395,800 that 1,3-diketones can be prepared by thermal rearrangement of the corresponding isomeric enol esters at a temperature of from 300° C. to 700° C. in a tube reactor, with the gaseous product mixture subsequently being condensed and the pure product being distilled off. A disadvantage is that free-radical mechanisms leading to undesirable by-products and to carbon formation proceed in reactions of this type and thus make it necessary to stop production for cleaning the reactor. These by-products reduce the selectivity and have to be separated off by distillation. DE-A2047320 (U.S. Pat. No. 3,794,686) describes a procedure in which a tetraalkyllead is added to the reaction mixture to prevent carbon deposition. The Derwent Abstract—JP-A63159337—describes the addition of water to improve the selectivity in the preparation of acetylacetone from isopropenyl acetate and at the same time, reduces the rate of carbon formation. However, a disadvantage is that the water thus introduced leads firstly to hydrolysis of the enol ester and secondly, to corrosion problems.

It is therefore an object of the invention to develop a process which gives a higher conversion at least equal selectivity and lower carbon formation without addition of promoters of water.

BRIEF DESCRIPTION OF THE INVENTION

The invention provides a process for preparing 1,3-diketones by means of thermal rearrangement of the corresponding isomeric enol esters in a tube reactor $1$ at a temperature of from 350° C. to 700° C. and subsequent cooling and work-up of the reaction product by distillation, wherein the tube reactor $1$ is not heated over its full length but only in a front section $1a$ which extends over a region from at least ¼ to at most ¾ of the total tube length, calculated from the reactor inlet, and the remaining unheated section $1b$ of the tube reactor $1$ is thermally insulated or cooled.

The invention further provides an apparatus for carrying out the process comprising a tube reactor $1$ having a front, un-insulated tube section $1a$ which extends over a region from at least ¼ to at most ¾ of the total tube length, calculated from the reactor inlet, and is provided with one or more heating elements $6$, and a downstream tube section $1b$ which is provided with cooling or insulation $2$ and is connected via a transfer tube $3$ to a column $4$ and is also provided with a line $5$ for the introduction of cooling liquid.

DETAILED DESCRIPTION OF THE INVENTION

Figure 1:
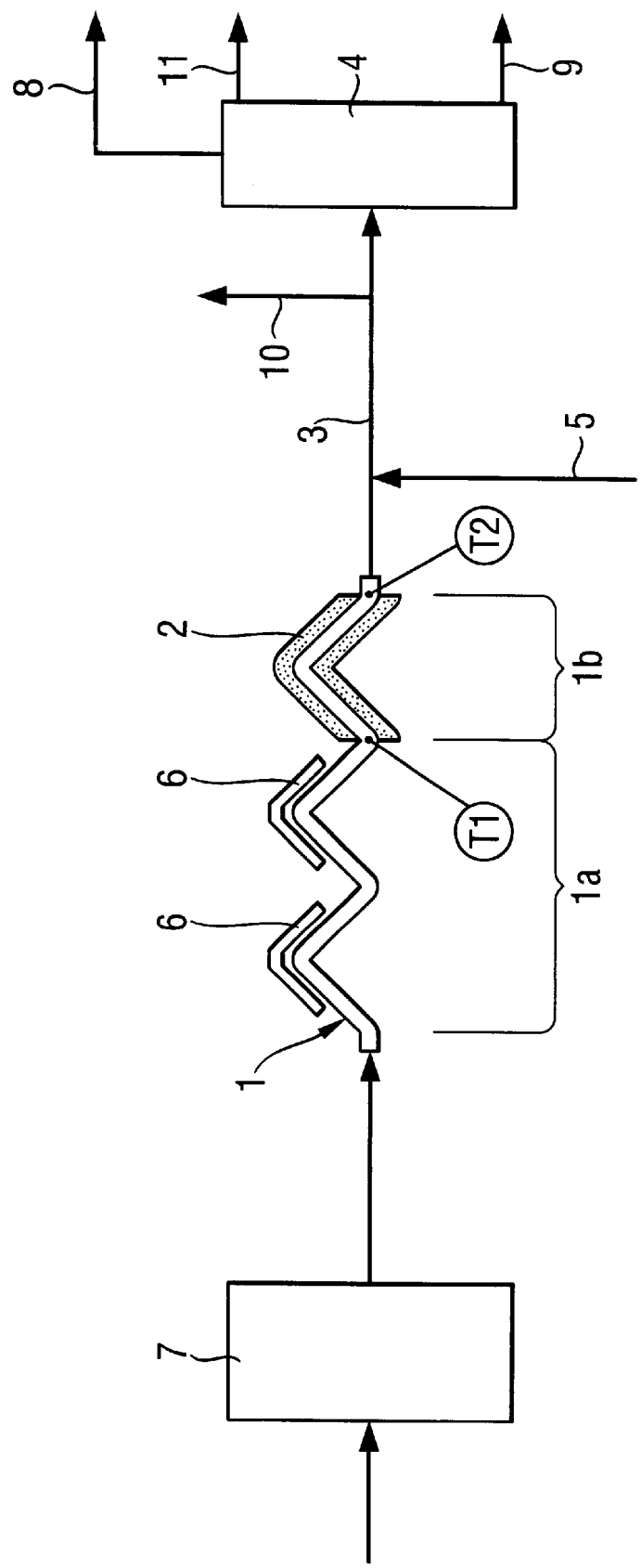
FIG. 1 is a diagrammatic representation of the process and apparatus of the invention.

The rearrangement to give the 1,3-diketones proceeds according to the following equation: $CR^1R^4= CR^2OCOR^3 \rightarrow R^2COCR^1R^4COR^3$ (1), where $R^4$, $R^2$, $R^3$ and $R^4$ in the enol esters of the formula $CR^1R^4= CR^2OCOR^3$ used as starting materials and in the 1,3-diketones of the formula $R^2COCR^1R^4COR^3$ may be identical or different and may each be hydrogen, a branched or unbranched alkyl group having from 1 to 8 carbon atoms or a phenyl group. Preferred starting materials are enol esters in which $R^1$, $R^2$, $R^3$ and $R^4$ are identical or different and are each hydrogen or an alkyl radical having from 1 to 3 carbon atoms.

A particularly preferred starting material is isopropenyl acetate (1-propen-2-ol acetate) with $R^1= R^4= H$ and $R^2= R^3= CH_3$, which is rearranged to form acetylacetone (2,4-pentanedione).

Prior to the rearrangement in the tube reactor, the starting material is heated to a temperature of from 90° C. to 110° C., preferably from 103° C. to 105° C., at a gauge pressure of from 0.8 bar to 1.5 bar, preferably at atmospheric pressure, and vaporized in a vaporizer $7$, preferably a circulation vaporizer or spiral tube vaporizer. The gaseous starting material is introduced into the tube reactor $1$.

The tube reactor $1$ is made of a corrosion-resistant material, usually stainless steel or fuzed quartz, preferably stainless steel. The tube reactor $1$ can be configured as a straight single tube, as a spiral tube or as a tube bundle. Preference is given to a single tube made up of tubular pieces arranged in a V-shape, if desired, concentrically aligned. The dimensions of the reaction tubes are preferably such that the downstream tube section $1b$ has a large volume/surface area ratio than the front tube section $1a$. Particular preference is given to a volume/surface area ratio of from 0.01 m to 0.4 m in the front tube section $1a$ and from 0.03 m to 0.6 m in the downstream tube section $1b$.

To provide heating, the tube reactor is equipped with one or more heating elements $6$, for example radiation heating or electric resistance heating, preferably electric resistance heating. If the tube reactor $1$ is a single tube made up of tubular pieces arranged in a V-shape, the tubular pieces can be heated individually. The tube section $1b$ which is not heated during the rearrangement reaction may, if desired, also be provided with one or more heating elements $6$. This embodiment makes it possible, if desired, to heat the tube briefly over its entire length prior to commencement of the rearrangement reaction in order to prevent condensation of the starting material on the tube wall, with associated encrustation, in the start-up phase.

The unheated section $1b$ of the tube reactor is preferably provided with thermal insulation $2$, for example a mineral wool mat, so as to enable the reaction to be carried out as adiabatically as possible in the region. If desired, this tube section $1b$ can also be provided with a cooling element.

The rearrangement reaction is carried out at atmospheric pressure and a temperature of from 350° C. to 700° C., preferably from 450° C. to 550° C. Energy input for heating occurs in the front section $1a$ of the reaction tube $1$, which section extends over a region of at least ¼ to at most ¾ of the total tube length, calculated from the reactor inlet. The heated tube section $1a$ preferably extends over a region of at least the front half to at most ¾ of the total tube length. Particular preference is given to heating the front two thirds of the reaction tube $1$. The energy input for heating this tube section $1a$ can be uniform. It is also possible to use a procedure in which more thermal energy is introduced in the front part of the heated tube section $1a$ than in the downstream part. For this purpose, from 50% to 150% more thermal energy is introduced in the front part than in the downstream part of the heated tube section $1a$. Preference is given to a process in which at least the front quarter to at most the front half of the heated tube section 1a is heated more strongly than the downstream part.

After reaching the rearrangement temperature in the heated part of the reactor 1, the rearrangement reaction is continued as adiabatically as possible. The reaction is preferably carried out so that, at atmosphere pressure, the temperature T1 at the transition from the heated tube section 1a to the unheated tube section 1b is in general from 470° C. to 510° C., particularly preferably from 480° C. to 500° C. Preference is given to reaction conditions under which the temperature T2 at the reactor outlet is higher than the temperature T1 at the transition between the heated and unheated zones. The temperature difference between T2 and T1 is particularly preferably at least 20° C.

In a further preferred embodiment, the reaction is carried out so that the starting material is brought to the reaction temperature in the heated tube section 1a within from 0.5 s to 1 s, is held at this temperature level in the unheated reaction zone 1b for a further 0.5 s–2 s, and the product mixture is subsequently cooled to from 100° C. to 200° C. within from 0.1 s to 1 s.

In general, the gaseous starting material or reaction mixture is passed through the reactor at a velocity of from 5 m/s to 20 m/s. After leaving the tube reactor, the reaction mixture is cooled. Cooling can be carried out by means of a heat exchanger, but the reaction mixture is preferably cooled by means of quenching.

Cooling is carried out in a transfer tube 3 between the tube reactor 1 and the column 4 for fractionation of the product mixture. The gaseous product mixture leaving the reactor is, in the preferred embodiment, cooled to a temperature of from 100° C. to 200° C., preferably from 110° C. to 130° C., by spraying a cooling liquid via line 5 into the transfer tube 3, immediately downstream of the reactor outlet, usually at a distance of up to 2 m, preferably at a distance of from 1 m to 2 m from the reactor outlet. The gaseous components which cannot be condensed at this temperature level, for example CO or $CO_2$, are taken off via line 10.

Suitable cooling liquids are, for example, water and the respective reaction product (1,3-diketone), the latter in, for example, the form of the bottom product from the column 4. Preference is given to using the bottom product from the column 4 as cooling liquid. The temperature of the cooling liquid is generally from 25° C. to 130° C., depending on which liquid is used as cooling liquid. Preference is given to a temperature range of from 50° C. to 80° C. If, in the preferred embodiment, the bottoms from the product fractionation are used as cooling liquid, they may be cooled beforehand to the specified temperature. In general, the weight ratio of product stream to quenching liquid is from 1:2 to 1:5. This procedure keeps the product stream at a temperature level of generally from 125° C. to 130° C., ensuring that, in the subsequent work-up of the product stream in the column 4, unreacted starting material can be separated off without further energy input either at the top via line 8 or via a separate line 11.

After quenching, the cooled product stream is conveyed to the column 4 for fratt ionation of the product mixture. Relatively low-boiling constituents are removed in a manner known per se at the top of the column via line 8 and unreacted starting material is removed via line 11, while the 1,3-diketone formed is obtained in the bottoms and can be passed via line 9 to further purification steps for removal of by-products.

The process of the invention surprisingly achieves, without addition of promoters or water, a significant increase in the yield and selectively, as well as a drastic minimization of carbonization. As comparison of Example 1 below with Comparative Example 2 shows, the yield is increased by 16% and the selectivity by 23%. The maintenance interval for cleaning out carbon deposits is increased by a factor of 16 from 3 weeks to 12 months. The energy input per amount of target product is significantly reduced compared to the prior art, since the heat of reaction obtained in the quench can be utilized for separating off the low boilers.

The process is illustrated below using the rearrangement of 1-propen-2-ol acetate (isopropenyl) acetate to acetylacetone (2,4-pentanedione) as an example, but applies analogously to the compounds specified in equation (1).

The apparatus is illustrated in FIG. 1 which shows a preferred embodiment of the invention.

EXAMPLE 1

500 kg/h of isopropenyl acetate were introduced via a circulation vaporizer 7 at atmospheric pressure into a resistance-heated tube reactor 1 which was made up of six tubular pieces in a concentric V arrangement having a length of 4.40 m each; the tubes in the front two thirds of the tube reactor had a diameter of 0.08 m (V/SA=0.02 m) and in the downstream third had a diameter of 0.2 m (V/SA=0.05). The tube reactor was heated in the front two thirds and insulated by a mineral wool mat in the downstream third. The thermal energy input was controlled so that the heat input in the front half (first third of the tube reactor 1) of the heated section 1a was twice as high as in the downstream half (second third of the tube reactor 1). The unheated zone 1b was insulated so that the radiation losses were so small that a temperature difference ΔT of 20° C. was established between the measurement points T1 at the end of the heated zone and T2 at the reactor outlet, with T2>T1. The product mixture leaving the reactor at a temperature of 530° C. was cooled to 128° C. immediately downstream of the reactor outlet by introducing a quenching stream into the transfer tube 3, using the bottom product from the column 4 as quenching liquid. Volatile, uncondensed product constituents were removed via line 10 and the cooled product stream was conveyed to the column 4 for further work-up. This process gave the performance characteristics shown in Table 1.

COMPARATIVE EXAMPLE 2

As in Example 1, 500 kg/h of isopropenyl acetate were introduced via a circulation vaporizer 7 at atmospheric pressure into the resistance-heated tube reactor 1. Unlike the procedure in Example 1, the tube reactor 1 was heated uniformly over its full length. The insulation around the reaction tube downstream of the heating zone was removed. After a short time, a temperature difference ΔT between T1 and T2 of 20° C. was established, with T2<T1. The product stream was cooled in a manner analogous to Example 1 using a product stream/quenching stream ratio of 1:1. The performance characteristics achieved using the procedure described are shown in Table 1.

TABLE 1

|  | Example 1 | Comp. Ex. 2 |
|---|---|---|
| Isopropenyl acetate feed | 500 kg/h | 500 kg/h |
| Total energy input | 108 KW | 108 KW |
| Energy distribution in the individual thirds of the reaction tube | 2:1:0 | 1:1:1 |

TABLE 1-continued

|  | Example 1 | Comp. Ex. 2 |
|---|---|---|
| Space-time yield of acetylacetone | 898 g/l xh | 777 g/l xh |
| Yield of acetylacetone based on isopropenyl acetate used (conversion) | 65.4% | 56.6% |
| Yield of acetylacetone based on isopropenyl acetate reacted (selectivity) | 85.2% | 69.1% |
| Ratio of product stream:quenching stream | 1:3 | 1:1 |
| Cleaning interval | 12 months | 3 weeks |

We claim:

1. A process for preparing 1,3-diketones by thermal rearrangement of a corresponding isomeric enol ester in a tube reactor at a temperature of from 350° C. to 700° C. and subsequent cooling and work-up of the reaction product by distillation, wherein the tube reactor consisting essentially of a heated first tube section which extends over a region from at least ¼ to at most ¾ of a total tube length, measured from the reactor inlet, and a remaining unheated thermally insulated, second tube section.

2. The process as claimed in claim 1, wherein the enol ester is of the formula $CR^1R^4 \equiv CR^2OCOR^3$, where $R^1$, $R^2$, $R^3$ and $R^4$ are each independently hydrogen, a branched alkyl group having 1 to 8 carbon atoms and an unbranched alkyl group having from 1 to 8 carbon atoms or a phenyl group.

3. The process as claimed in claim 1, wherein isopropenyl acetate is rearranged to form acetylacetone.

4. The process as claimed in claim 1, wherein more thermal energy is introduced in a front portion of the first tube section than in a downstream portion of the first tube section.

5. The process as claimed in claim 1, wherein, at atmospheric pressure, the temperature T1 at a transition point from the first tube section to the unheated second tube section, is from 470° C. to 510° C.

6. The process as claimed in claim 1, wherein a temperature T2 at an outlet of the second tube section is higher than a temperature T1 at a transition point between the heated first tube section and the unheated second tube section.

7. The process as claimed in claim 1, wherein the gaseous product mixture leaving the reactor is cooled to a temperature of from 100° C. to 200° C. by contact with a cooling liquid immediately downstream of a reactor outlet from the second tube section.

8. The process as claimed in claim 7, wherein the cooling liquid comprises water or the reaction product.

9. The process as claimed in claim 8, wherein the ratio by weight of product stream to cooling liquid is from 1:2 to 1:5.

10. The process as claimed in claim 1, wherein the reaction is carried out so that the isomeric enol ester is brought to the reaction temperature in the heated first tube section within from 0.5 s to 1 s, is held at the reaction temperature in the unheated second tube section for a further 0.5 s–2 s, and the reaction product is subsequently cooled to from 100° C. to 200° C. within from 0.1 s to 1 s.

11. The process as claimed in claim 10, wherein the reaction product is cooled to a temperature level of from 125° C. to 130° C.

12. The process as claimed in claim 2, wherein more thermal energy is introduced in the front portion of the first tube section than in a downstream portion of the first tube section.

13. The process as claimed in claim 2, wherein, at atmospheric pressure, the temperature T1 at a transition point from the first tube section to the unheated second tube section is from 470° C. to 510° C.

14. The process as claimed in claim 2, wherein a temperature T2 at an outlet of the second tube section is higher than a temperature T1 at a transition point between the heated first tube section and the unheated second tube section.

15. The process as claimed in claim 2, wherein the gaseous product mixture leaving the reactor is cooled to a temperature of from 100° C. to 200° C. by contact with a cooling liquid immediately downstream of a reactor outlet from the second tube section.

16. The process as claimed in claim 5, wherein a temperature T2 at an outlet of the second tube section is higher than a temperature T1 at a transition point between the heated first tube section and the unheated second tube section.

17. The process as claimed in claim 5, wherein the gaseous product mixture leaving the reactor is cooled to a temperature of from 100° C. to 200° C. by contact with a cooling liquid immediately downstream of a reactor outlet from the second tube section.

* * * * *

UNITED STATES PATENT AND TRADEMARK OFFICE
CERTIFICATE OF CORRECTION

PATENT NO. : 6,310,258 B1
DATED : October 30, 2001
INVENTOR(S) : Dempf et al.

It is certified that error appears in the above-identified patent and that said Letters Patent is hereby corrected as shown below:

Column 5,
Lines 18 and 40, delete "C." and insert therefor -- C -- (2 occurrences).
Line 26, delete "≡" and insert therefor -- = --.

Column 6,
Lines 1, 14, 33 and 43, delete "C." and insert therefor -- C -- (2 occurrences).
Lines 14 and 17, "C." (first occurrence) and insert therefor -- C --.

Signed and Sealed this

Thirteenth Day of August, 2002

Attest:

Attesting Officer

JAMES E. ROGAN
*Director of the United States Patent and Trademark Office*